US006998388B1

(12) United States Patent
Cockerill et al.

(10) Patent No.: US 6,998,388 B1
(45) Date of Patent: Feb. 14, 2006

(54) HIGH DENSITY LIPOPROTEIN AGAINST ORGAN DYSFUNCTION FOLLOWING HAEMORRHAGIC SHOCK

(75) Inventors: Gillian Cockerill, London (GB); Norman Miller, London (GB); Christoph Thiemermann, London (GB); Michelle MacDonald, London (GB)

(73) Assignee: ZLB Behring AG, Bern (CH)

( * ) Notice: Subject to any disclaimer, the term of this patent is extended or adjusted under 35 U.S.C. 154(b) by 358 days.

(21) Appl. No.: 10/069,157

(22) PCT Filed: Aug. 16, 2000

(86) PCT No.: PCT/GB00/03182

§ 371 (c)(1),
(2), (4) Date: May 24, 2002

(87) PCT Pub. No.: WO01/13939

PCT Pub. Date: Mar. 1, 2001

(30) Foreign Application Priority Data

Aug. 19, 1999 (GB) .................................... 9919713

(51) Int. Cl.
*A61K 38/00* (2006.01)
(52) U.S. Cl. ........................................ 514/21; 530/359
(58) Field of Classification Search ................ 530/300, 530/359; 514/2, 21
See application file for complete search history.

(56) References Cited

U.S. PATENT DOCUMENTS 5,780,592 A * 7/1998 Mullner et al. ............. 530/359

FOREIGN PATENT DOCUMENTS

| EP | 0 780 128 A2 | 6/1997 |
| JP | 08198406 | 7/1996 |
| WO | WO97/06822 | 2/1997 |

OTHER PUBLICATIONS

High-Density Lipoprotein: Multipotent Effects on Cells of the Vasculature, International Review of Cytology, vol. 188, (0074-7696/99, Gillian W. Cockerill and Steven Reed, pp. 257-275 (10 sheets).
High-Density Lipoprotein: Multipotent Effects on Cells of the Vasculature, International Review of Cytology, vol. 188, (0074-7696/99, Gillian W. Cockerill and Steven Reed, pp. 276-297 (11 sheets).
Ischemia-Reperfusion Arrhythmias and Lipids: Effect of Human High- and Low-Density Lipoproteins on Reperfusion Arrhythmias, Cardiovascular Drugs and Therapy, 1991; 5:269-276, pp. 269-277 (4 sheets).
High-Density Lipoproteins Differentially Modulate Cytokine-Induced Expression of E-Selection and Cyclooxygenase-2, pp. 910-917 (Feb. 9, 1998) (4 sheets).

* cited by examiner

*Primary Examiner*—Bruce R. Campbell
*Assistant Examiner*—Ray Teller
(74) *Attorney, Agent, or Firm*—Flynn, Thiel, Boutell & Tanis, P.C.

(57) ABSTRACT

Use of high density lipoprotein and/or derivatives in the manufacture of a medicament for the prevention or treatment of organ dysfunction following ischaemia and reperfusion injury. In particular, the medicament may be for the treatment of end stage organ injury or failure.

8 Claims, 15 Drawing Sheets

FIGURE 1

FIGURE 1A Heart rate (beats per min) in all experimental groups before hemorrhage (Baseline) and 1,2,3, and 4 h after resuscitation.

| Group | n | Baseline | Resuscitation Time (h) | | | |
|---|---|---|---|---|---|---|
| | | | 1 | 2 | 3 | 4 |
| 1. SHAM | 9 | 381 ± 15 | 369 ± 11 | 385 ± 13 | 384 ± 13 | 377 ± |
| 2. SHAM-recHDL | 4 | 416 ± 10 | 387 ± 12 | 376 ± 8 | 393 ± 6 | 380 ± |
| 3. HS | 9 | 386 ± 11 | 417 ± 10 | 423 ± 20 | 398 ± 24 | 372 ± |
| 4. HS-recHDL | 9 | 364 ± 13 | 386 ± 13 | 407 ± 10 | 391 ± 14 | 378 ± |
| 5. HS-nHDL | 7 | 388 ± 11 | 381 ± 15 | 369 ± 8 | 356 ± 12 | 340 ± |

Group 1: Rats were subjected to the surgical procedure without causing a hemorrhage and treated with vehicle for HDLs (saline, 1ml/kg i.v. bolus followed by an infusion of 1.5 ml/kg/h i.v.; n=9); Group 2: Rats were subjected to the same surgical procedure as group 1 but were treated with recHDLs (80mg/kg i.v. bolus injection, followed by an infusion of saline 1.5ml/kg/h i.v., n=4); Group 3: Rats were subjected to a hemorrhage for 1.5 h and upon resuscitation with the shed blood were given an infusion of saline (1.5ml/kg/h i.v., n=9); Group 4: Rats were subjected to the same procedure as Group 3 but treated with recHDLs (80mg/kg i.v.bolus injection, followed by an infusion of saline 1.5ml./kg/h i.v., n=9); Group 5: Rats were treated in the same way as Group 4, but were given nHDLs instead of recHDLs prior to resuscitation. There were no significant differences in the hear rates between any of the experimental groups.

HIGH DENSITY LIPOPROTEIN AGAINST ORGAN DYSFUNCTION FOLLOWING HAEMORRHAGIC SHOCK

The present invention relates to the manufacture of medicaments for protecting against organ damage following haemorrhagic shock, using high-density lipoproteins (HDLs) and derivatives thereof. In particular, it relates to manufacture of medicaments for treatment and prevention of end-stage organ failure following haemorrhagic shock.

Many victims of sudden physical injury (for example, traffic accident victims) die because of end-stage organ failure. In patients with this condition, biochemical and biological changes (such as haemodynamic changes and microthrombus formation) occur in the blood and organs (such as liver and kidneys) due to shock and blood loss; this is a different action to "endotoxic" shock which arises due to bacterial infection. If end-stage organ failure is not halted or prevented, it will lead to permanent organ damage and death of the patient. There is a need for a pharmaceutical agent which can be administered as soon as possible after the physical injury, preferably at the site of the accident in order to prevent end stage organ failure, and which can also be used subsequently while transporting the victim from the accident site to casualty/hospital, and while the physical wounds are being treated.

High-density lipoproteins (HDLs) form a range of lipoprotein particles found in normal serum. Mature HDL particles are present in the form of a globular structure containing proteins and lipids. Within the outer layer of these particles are the more polar lipids, phospholipids and free cholesterol, all having charged groups pointing outwards towards the aqueous environment. The more hydrophobic lipids, such as esterified cholesterol and triglycerides, reside in the core of the particle. Newly formed, or nascent, HDL particles lack the lipid core and are discoidal in shape. Protein components are embedded in the outer layer. The main protein component is apolipoprotein A-I (apo A-I), with smaller amounts of apo A-II, apo A-IV, apo CIII, apo D, apo E and apo J. Various other proteins reside on the HDL particle, such as lecithin-cholesterol acetyl transferase, PAF acetylhydrolase and paraoxonase.

The binding of activated leukocytes to the endothelium is the earliest observable cellular event in a number of acute and chronic inflammatory diseases. This binding is mediated by the expression of adhesion molecules on the surface of the endothelial cells which bind to corresponding molecules of similar function on leukocytes. Recently we have shown that pre-treatment of endothelial cells, in vitro, with HDL was able to inhibit the cytokine-induced expression of these adhesion molecules (Cockerill G W, Rye K-A, Gamble J R, Vadas M A, Barter P J. Arterioscler Thromb. Vasc. Biol. 1995, 15: 1987–1994 1995, Cockerill G W Reed S. Int. Rev. Cytol: A survey of cell biology 1999). In addition, we have recently shown that HDL can inhibit cytokine-induced adhesion molecule expression in an acute inflammatory model in the pig (Cockerill et al., submitted 1999). The antiflammatory effects of HDL have thus been demonstrated in these models where cells/animals are pre-treated with lipoprotein.

End-stage organ failure following haemorrhagic shock results from the adhesion of polymorphonuclear leukocytes (PMNs) to the endothelium following their activation caused by ischaemia and reperfusion injury. We have now found that administration of HDL or derivatives thereof prevents end-stage organ failure following haemorrhagic shock.

According to the present invention high density lipoprotein and/or a derivative thereof is used in the manufacture of a medicament for the prevention or treatment of organ dysfunction following haemorrhagic shock.

Preferably, the medicament is for the treatment of end-stage organ injury or failure.

We have shown that, following haemorrhagic shock, HDL is able to perturb the damaging effects when given after the initial hypovolaemia has occurred. Our work suggests that at physiological levels (both in vitro and in vivo), native HDL particles are active in inhibiting the expression of adhesion proteins on endothelial cells. Prevention of expression of adhesion proteins on endothelial cells prevents binding of PMNs to the endothlium; thus administration of HDL prevents end-stage organ failure.

The high density lipoprotein may be the component of HDL that inhibits adhesion to the endothelial cells and subsequent activation of leukocytes or a derivative, molecule, homologue, or mimic thereof.

The inhibiting effect is not only present in venous endothelial cells but also on arterial endothelial cells and is independent of the nature of the lipid present in the HDL particles. Two effector molecules mediate the inhibitory effect namely apolipoprotein A-I (apo A-I) and apolipoprotein A-II (apo A-II) (Brouillette C. G. and Anatharamaiah G. M. Biochem. Biophys. Acta. 1256: 103–129. 1995; Massey J. B., Pownall H. J. Biochem. Biophys Acta. 999: 111–120. 198); these two molecules have different efficacy of inhibition.

Preferably, the high density lipoprotein or derivative thereof is a peptide or protein derivative of the sequence of apo A-I or apo A-II, or a peptide or protein derivative functionally homologous to the active portions of apo A-I or apo A-II.

Preferably, the high density lipoprotein is reconstituted HDL. The term "reconstituted HDL" means HDL composed of a lipid or lipids in association with at least one of the apolipoproteins of HDL. The components may be derived, for example, from blood, or produced by recombinant technology.

The medicament may be administered to a patient in any conventional manner. Preferably the medicament is administered intravenously. Preferably, the medicament is administered using saline as a vehicle.

Preferably the medicament is provided in a portable dispenser, for example, for use at the site of an accident.

According to the invention in another aspect there is provided a method of treatment of organ dysfunction following haemorrhagic shock in a human patient which comprises the step of administering to a patient reconstituted high density lipoprotein and/or a derivative thereof in pharmaceutically acceptable form.

The present invention will now be illustrated with reference to the attached drawings in which:

FIG. 1A shows a Table of heart rate in beats per minute (bpm) in all experimental groups studied before the haemorhhage −1.5 h and 1, 2, 3 and 4 h after resuscitation, Group 1 (SHAM): Rats were subjected to the surgical procedure without causing a haemorrhage and treated with a vehicle for HDL (saline, 1 ml/kg i.v. bolus followed by an infusion of 1.5 ml/kg/h i.v.; n=9); Group 2 (SHAM-recHDL): Rats were subjected to the same surgical procedure as Group 1 but treated with recHDLs (reconstituted HDLs) (80 mg/kg i.v. bolus injection followed by an infusion of saline 1.5 ml/kg/h i.v. n=4); Group 3 (HS): Rats were subjected to a haemorrhage for 1.5 h and upon resuscitation with the shed blood were given an infusion of 1.5 ml/kg/h i.v., n=9); Group 4 HS-recHDL: rats were subjected to the same procedure as group 3 but treated with recHDLs (80 mg/kg i.v. bolus injection followed by an infusion of saline 1.5 ml/kg/h i.v.; n=9); and Group 5 (HS-nHDL): rats were treated in the same way as Group 4, but were given nHDLs instead of recHDLs prior to resuscitation.

As a demonstration of an embodiment of the invention, Experiment 1 describes the effects of human high-density lipoprotein (HDL) on the circulatory failure and multiple organ dysfunction injury (MODS) such as renal dysfunction and liver dysfunction caused by severe haemorrhage and resuscitation in the anesthetised rat. It should be noted that this is a model of end stage organ failure generated by haemorrhagic shock, and is not known to be a result of endotoxin release.

All experiments described herein were performed in adherence to the National Institute of Health guidelines on the use of experimental animals and in adherence to *Home Office Guidance on the Operation of the Animals (Scientific Procedures) Act* 1986, published by HMSO, London.

Experiment 1

The study was carried out on Wistar rats (Tuck, Rayleigh, Essex, UK) weighing 250 mg–320 g receiving a standard diet and water ad libitum. All animals were anaesthetised with thiopentone (120 mg/kg i.p.) and anaesthesia was maintained by supplementary injections of thiopentone as required. The trachea was cannulated to facilitate respiration and rectal temperature was maintained at 37° C. with a homeothermic blanket. The right femoral artery was catheterised and connected to a pressure transducer (Senso-Nor 840, Senso-Nor, Horten, Noway) for the measurement of phasic and mean arterial blood pressure (MAP) and heart rate (HR). These were displayed on a data acquisition system (MacLab 8e, ADI Instruments, Hasting, UK) installed on an Apple Macintosh computer. The right carotid artery was cannulated to bleed the animals (see hereafter). The jugular vein was cannulated for the administration of drugs. The bladder was also cannulated to facilitate urine flow and to prevent the possibility of development of post-renal failure. Upon completion of the surgical procedure, cardiovascular parameters were allowed to stabilise for 15 mins. Then, blood was withdrawn from the catheter placed in the carotid artery in order to achieve a fall in MAP to 50 mmHg within 10 mins. Thereafter, MAP was maintained at 50 mmHg for a total period of 90 mins by either withdrawal (during the compensation period) or re-injection of blood. It should be noted that in these experiments, the amount of shed blood re-injected during the 90 min period of haemorrhage did not exceed 10% of the total amount of the blood withdrawn. The amount of blood withdrawn for rats subjected to haemorrhage and treated with vehicle (control group) was 7.0±0.4 ml (SD); the amount of blood withdrawn from rats subjected to haemorrhage and treated with HDL (treatment group) was 7.0±0.3 ml (p>0.05). At 90 min after initiation of haemorrhage, the shed blood and an equivalent volume of Ringer lactic solution was re-injected into the animal.

Figure 1:
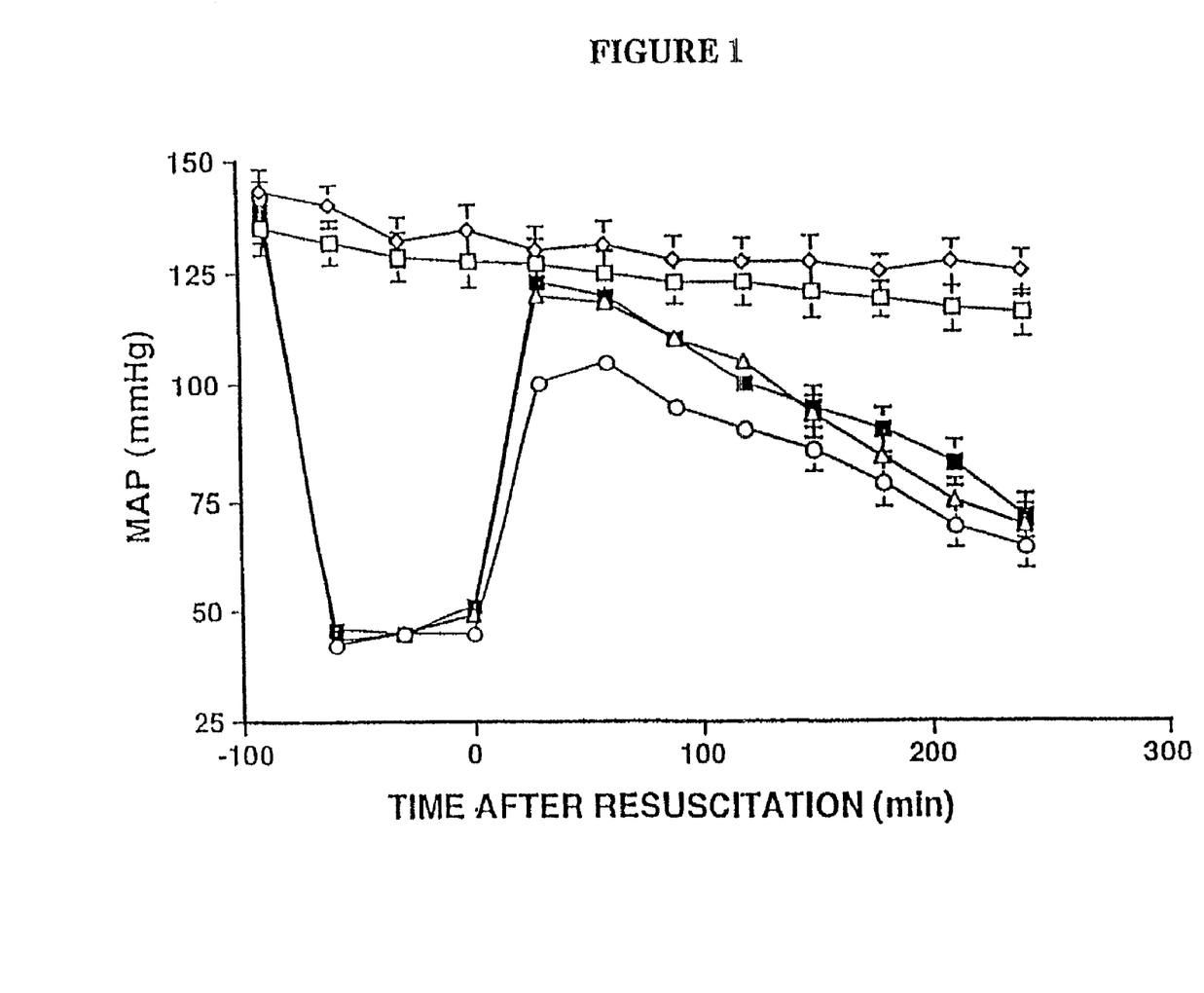
FIG. 1 shows alterations in mean arterial blood pressure (MAP) in rats subjected to (i) the surgical procedure without causing a haemorrhage and treated with vehicle for HDL (SHAM, open diamonds, saline, 3 mg/kg i.v. bolus; n=9) or with recHDL (SHAM-recHDL open square, 80 mg/kg i.v. bolus injection, n=9) or (ii) haemorrhage for 1.5 h and upon resuscitation with the shed blood, control rats were treated with the vehicle (HS open circles, saline 3 ml/kg i.v. bolus; n=10), recHDL (HS-recHDL filled squares, 80 mg/kg i.v. bolus injection, n=9) or nHDL (HS-nHDL open triangle, 80 mg/kg i.v. bolus injection) [nHDL=native HDL; rHDL or recHDL is reconstituted HDC]
Figure 1A:
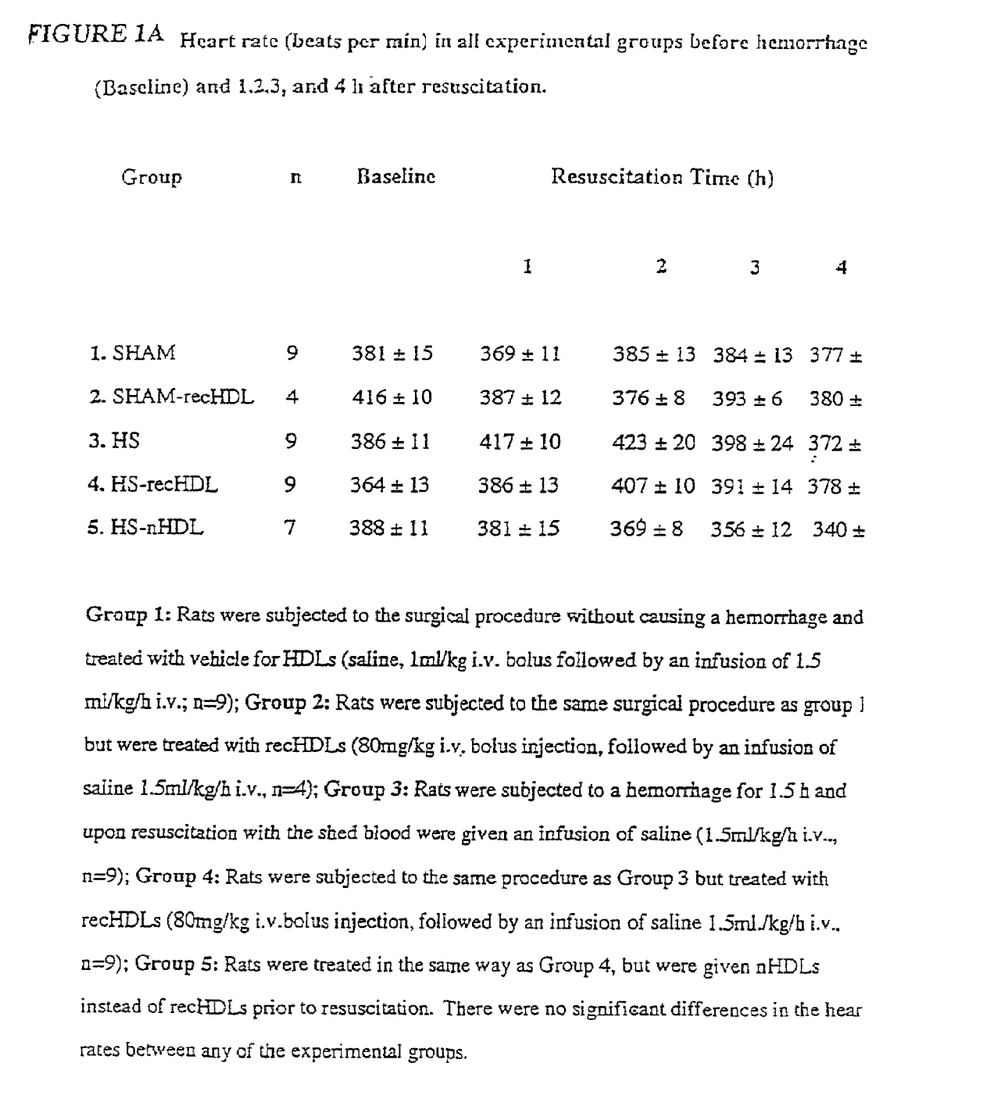
Figure 2A:
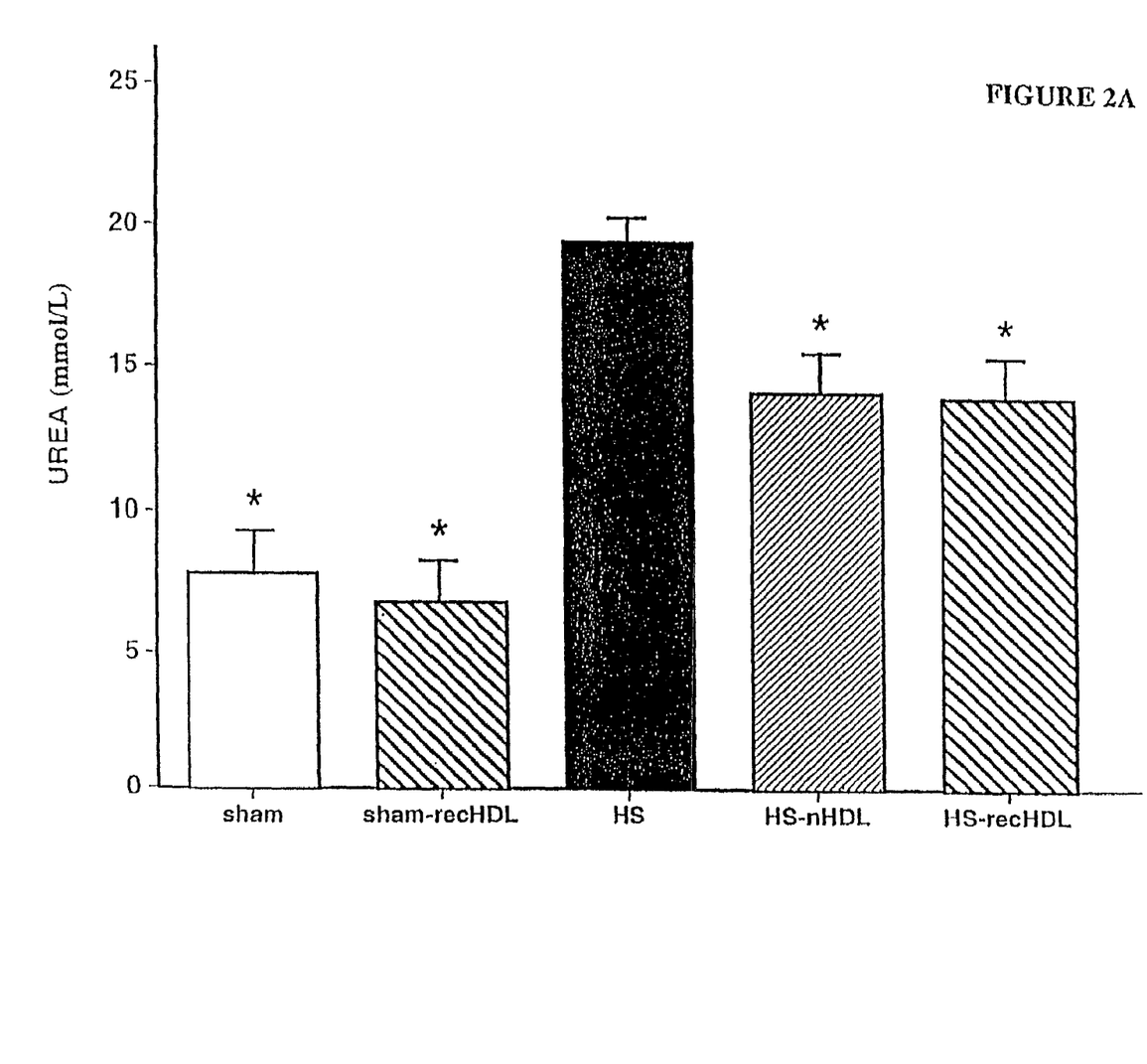
FIG. 2 shows plasma levels of (A) urea, (B) creatine, (C) AST, (D) ALT, (F) creatinine kinase (CK) and (E) lipase in rats subjected to the surgical procedure and experiment 2 described below.
Figure 2B:
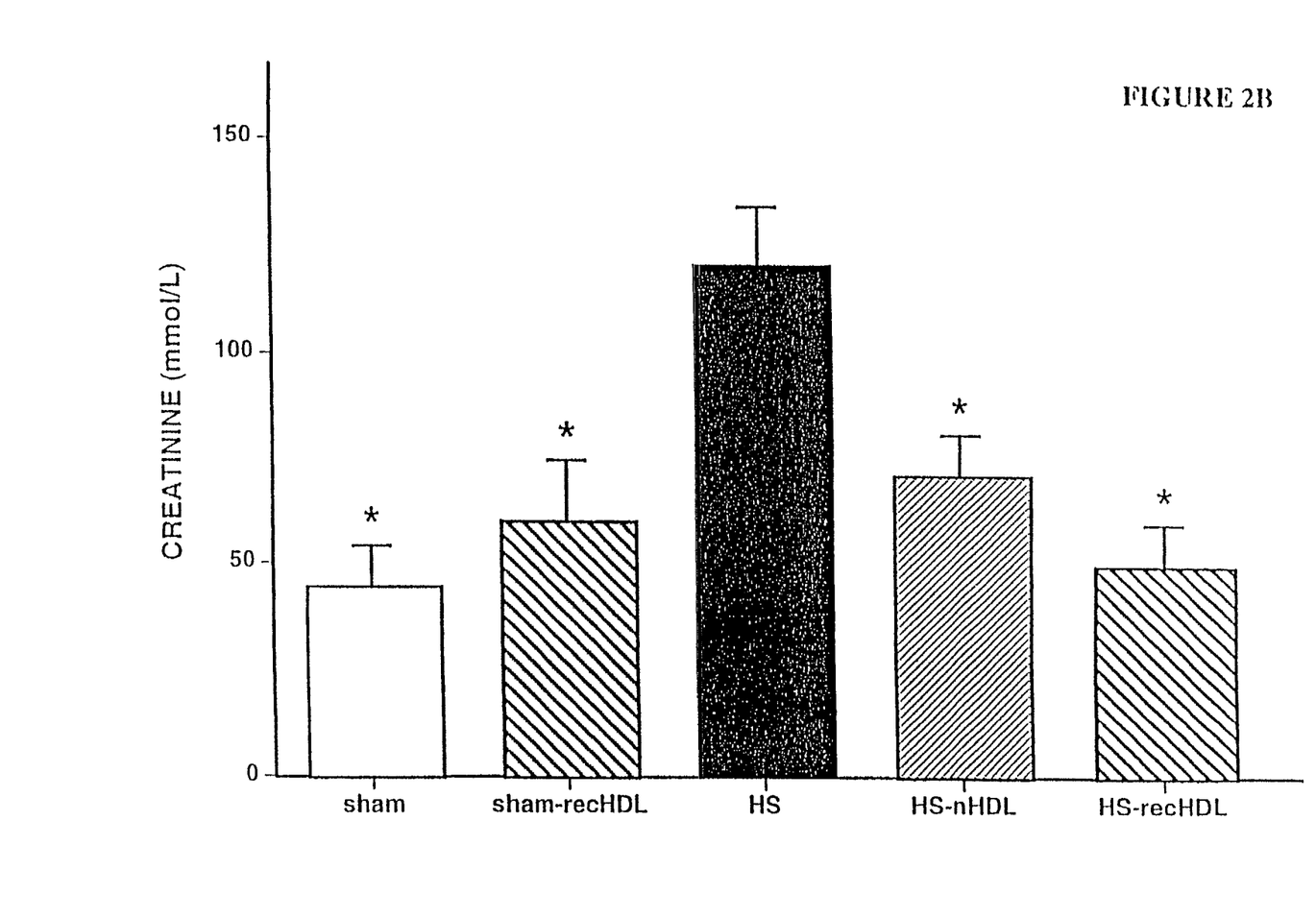
Figure 2C:
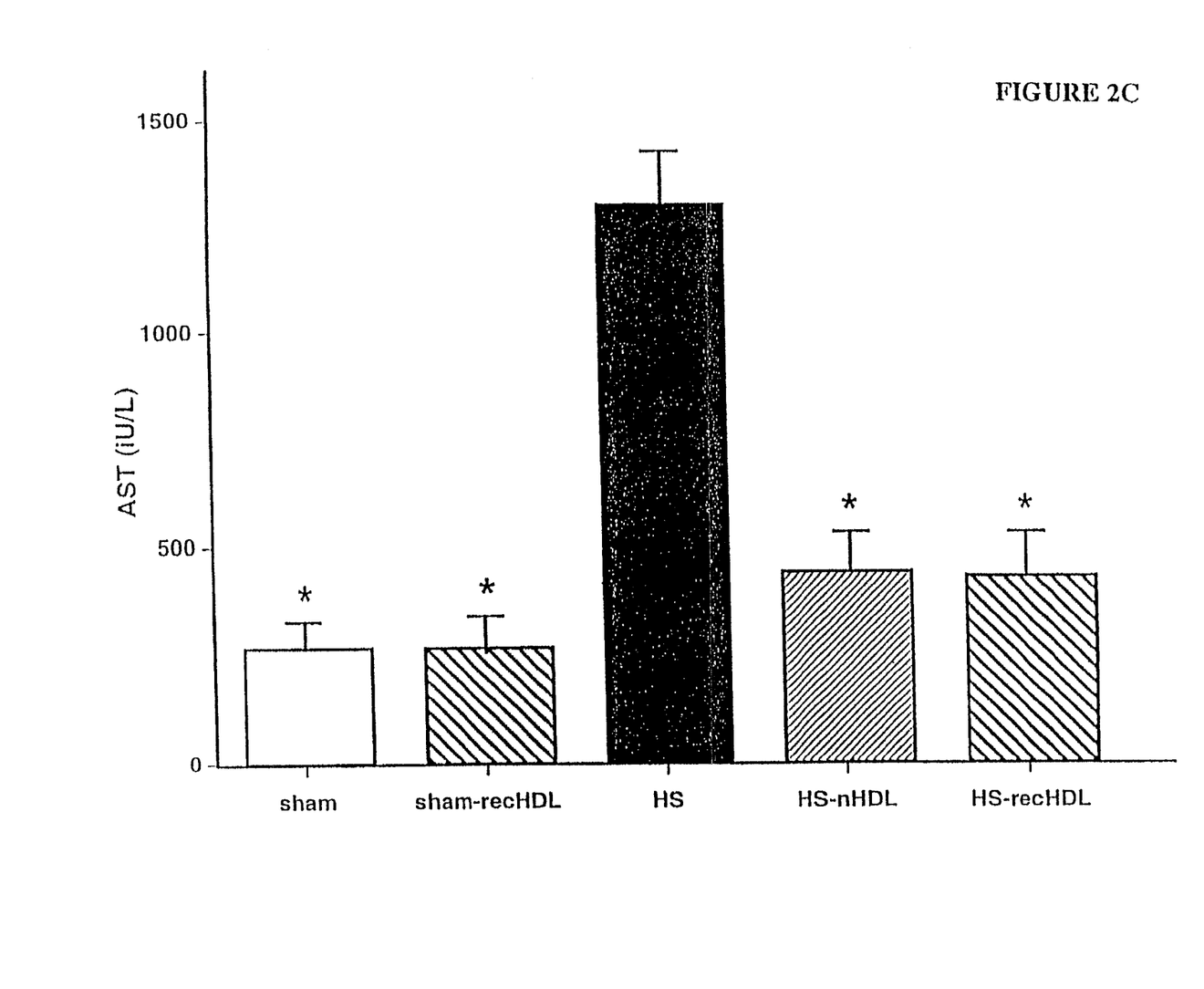
Figure 2D:
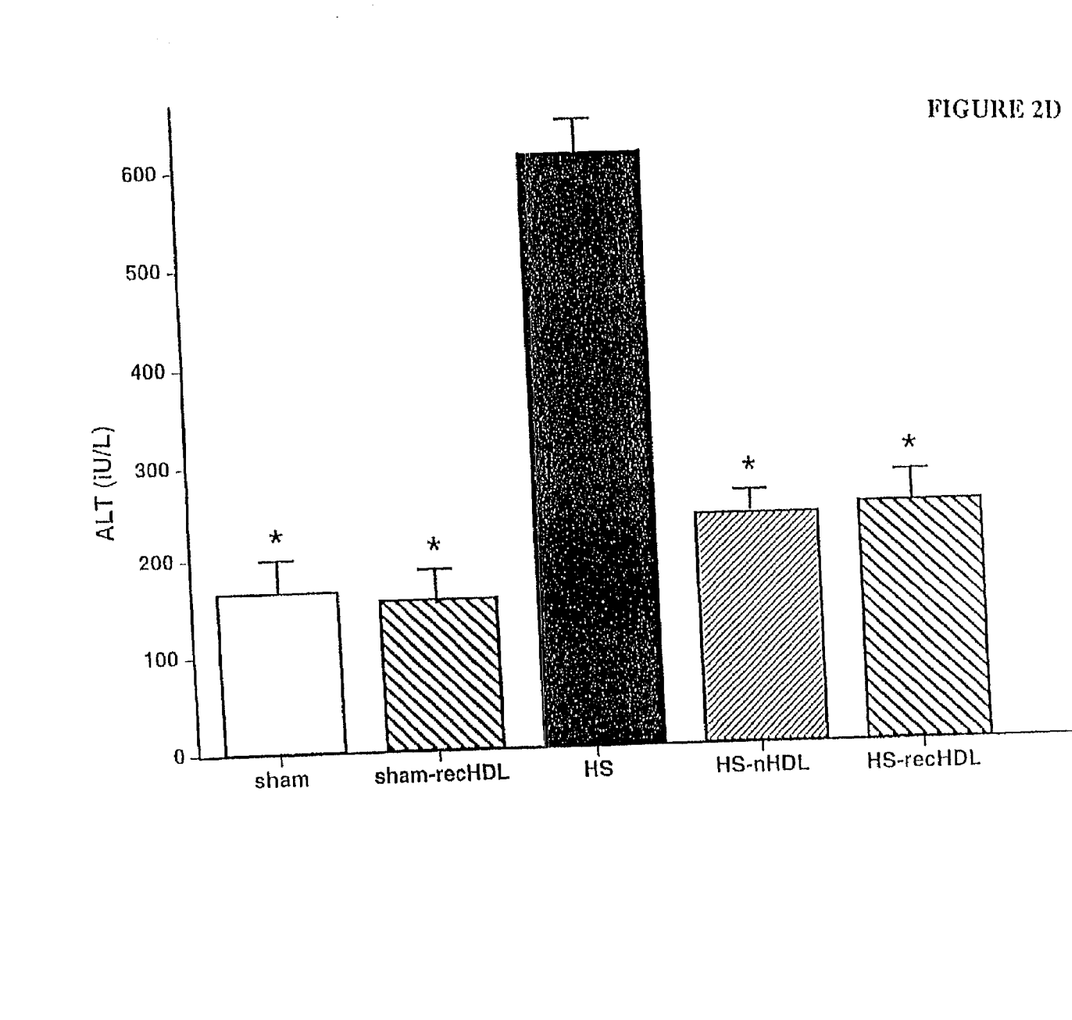
Figure 2E:
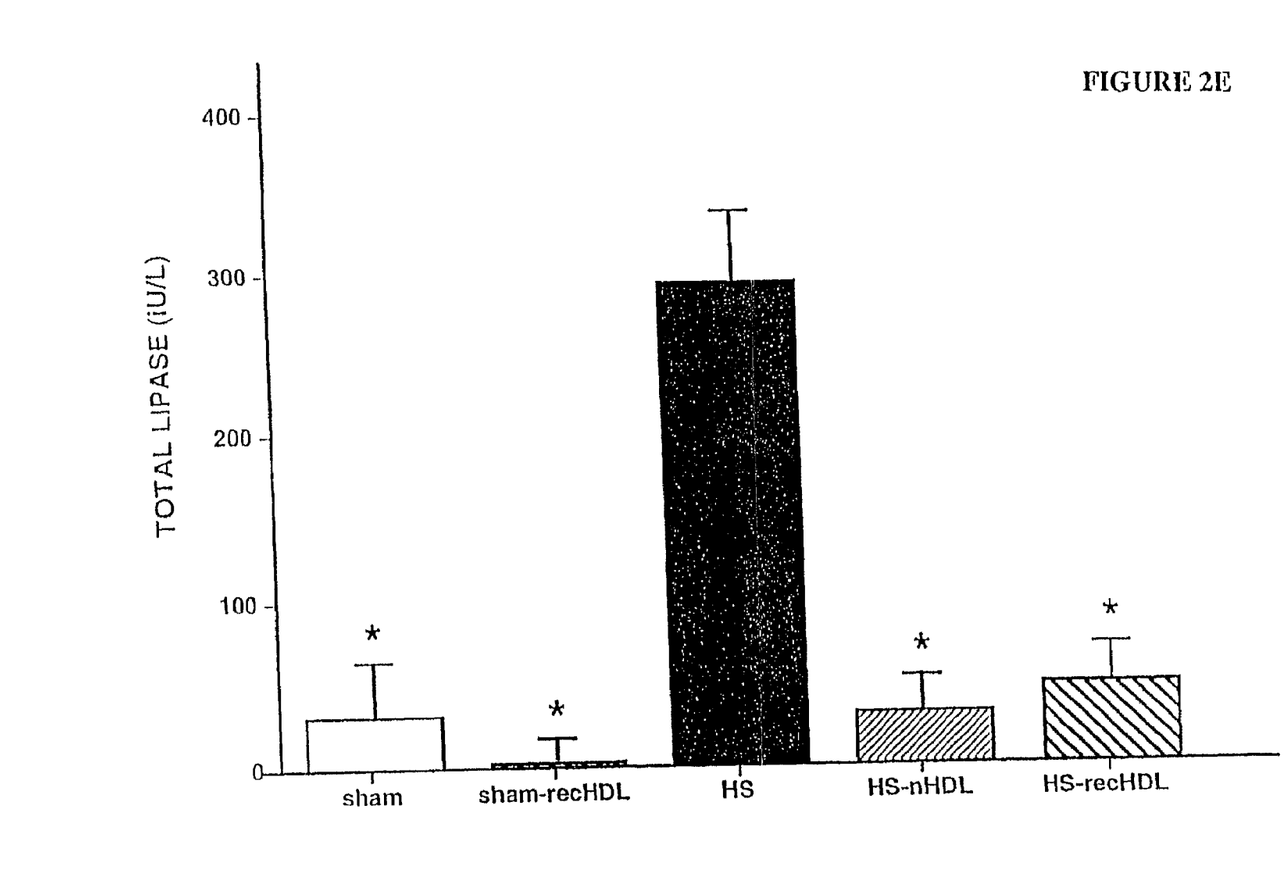
Figure 2F:
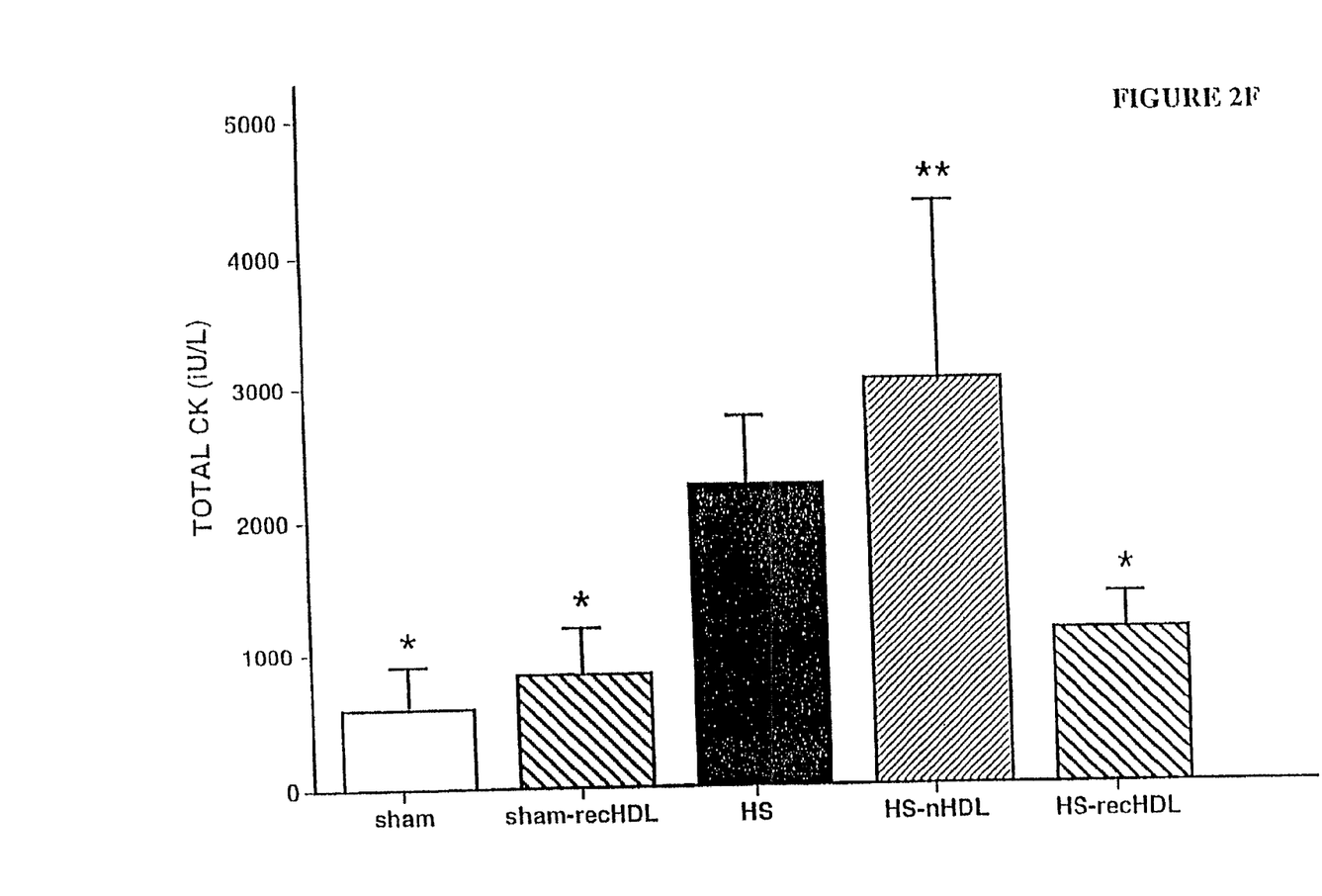

The results are shown in FIGS. 1, 1A (Table 1), 2, 3 and 4.

FIG. 2 shows plasma levels of (A) urea, (B) creatinine, (C) AST, (D) ALT, (F) creatinine kinase (CK) and (E) lipase in rats subject to (i) SHAM the surgical procedure without causing a haemorrhage and treated with vehicle for HDL (sham+saline, saline, 3 ml/kg i.v. bolus i.v.; n=9) or with reconstituted HDL (sham+recHDL; 80 mg/kg i.v. bolus injection, n=4, or (ii) haemorrage for 1.5.h and upon resuscitation with the shed blood, control rats were treated with the vehicle (hs{+saline}, saline 3 ml/kg i.v. bolus n=9), reconstituted HDL (hs+recHDL, 80 mg/kg i.v. bolus injection, n=9) or nHDL (HS–nHDLC). The administration regimes are detailed more fully in the text accompanying FIG. 1A. Haemorrhage and resuscitation resulted in significant increases in the serum levels of urea and creatinine (n=9), as demonstrated by the increase in urea and creatine concentration between "sham" and hs (control). This renal dysfunction was attenuated by the administration (5 mins prior to resuscitation) of HDL (80 mg/kg. i.v., n=9; p,0.05; ANOVA followed by Dunnett's test for multiple comparisons), as demonstrated by the concentration of urea and creatinine for "HS+recHDL" and HS–nHDL. Similarly, HOL attenuated the liver injury (as monitored by a rise in serum AST and ALT)—(C) and (D)—and the pancreatic injury (as measured by a rise in serum lipase—(E)) caused by haemorrhage and resuscitation. In contrast, recHDL and nHDL did not affect the delayed circulatory failure associated with haemorrhage and resuscitation (see FIG. 1 and FIG. 1A (Table 1)). Administration of recHDL to rats which were not subjected to haemorrhage did not result in the alterations in the serum levels of urea, creatinine, AST, ALT or lipase (n=4) and, hence, was not toxic at the dose used.

Organ Dysfunction as Measured by the Decree of Disruption of Tissue Architecture was Reduced by Treatment with HDLs.

Light microscopy. Organ (lung, kidney and small intestine) biopsies were taken at the end of Experiment 1 and fixed for one week in buffered formaldehyde solution (10% in PBS) at ambient temperature, dehydrated by graded ethanol, and embedded in Paraplast™ (Sherwood Medical, Mahwah, N.J., USA). Sections (7 µm thick) were deparaffinised with xylene, and stained using either Van Gieson's Trichrome or Fuchsin, and examined using light microscopy (Dialux 22, Leitz).

Figure 3:
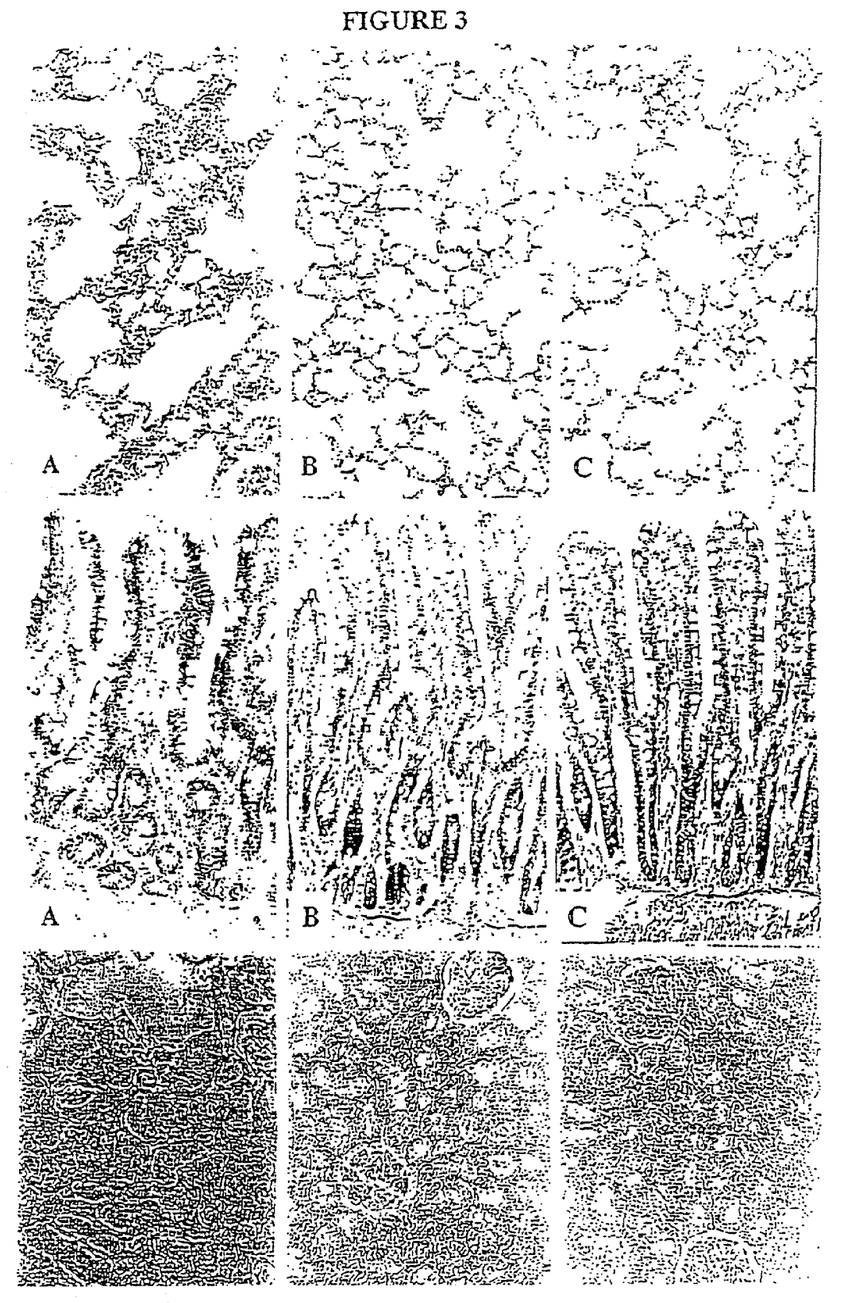
FIG. 3 shows the effect of HDL infusion on histological sections from lung, gut and kidney following haemorrhagic shock.

FIG. 3 shows photomicrographs of representative sections of lung (upper panels), small intestine (middled panels), and kidney (lower panels) from animals following haemorrhage for 90 min. and given vehicle (saline) along with shed blood at the beginning of resuscitation (A), nHDLCs (80 mg/kg i.v. bolus injection) prior to resuscitation (B), or recHDLs (80 mg/kg i.v. bolus injection prior to resuscitation (C).

Sections were visualised using Van Geison's trichrome stain. Original magnification×100.

When compared to organs obtained from sham-operated rats, which had not been subjected to haemorrhage and resuscitation (data not shown), FIG. 3 demonstrates that the lung (top panels), small intestine (middle panels) and kidney (bottom panels), when subjected to haemorrhage and resuscitation (A), show oedema with loss of normal tissue structure. In contrast, organs from animals which had received nHDLs (B) or recHDLs (C) prior to resuscitation showed no significant change in morphology, and were not significantly different from the sham-operated rats (not shown).

HDLs Reduced Neutrophil Infiltration into Lungs and Kidneys Following Haemorrhage and Resuscitation.

Myeloperoxidase (MPO) activity, an indicator of polymorphonuclear leukocyte (PMN) accumulation was determined as previously described (Anderson, B. O., Brown, J. M., Shanley, P. F., Benserd, D. D., and Harken, A. H. (1991 Marginating neutrophils are reversibly adherent to normal lung endothelium. Surgery 109.51–61)). Samples of lung and kidney were obtained and weighed. Each piece of tissue was homogenized in a solution containing 0.5% hexadecyl-trimethyl-ammonium bromide dissolved in 10 mM potassium phosphate buffer (pH 7.0) and centrifuged for 30 min at 20,000×g at 4° C. An aliquot of the supernatant was then allowed to react with a solution of tetra-methyl-benzidine (1.6 mM) and 0.1 mM $H_2O_2$. The rate of change in absorbance was measured spectrophotometrically at 650 nm. 1 mÜ of MPO activity was defined as the quantity of enzyme degrading 1 µmol of peroxidase per min at 37° C., and was expressed in mÜ per mg of wet tissue.

Figure 4A:
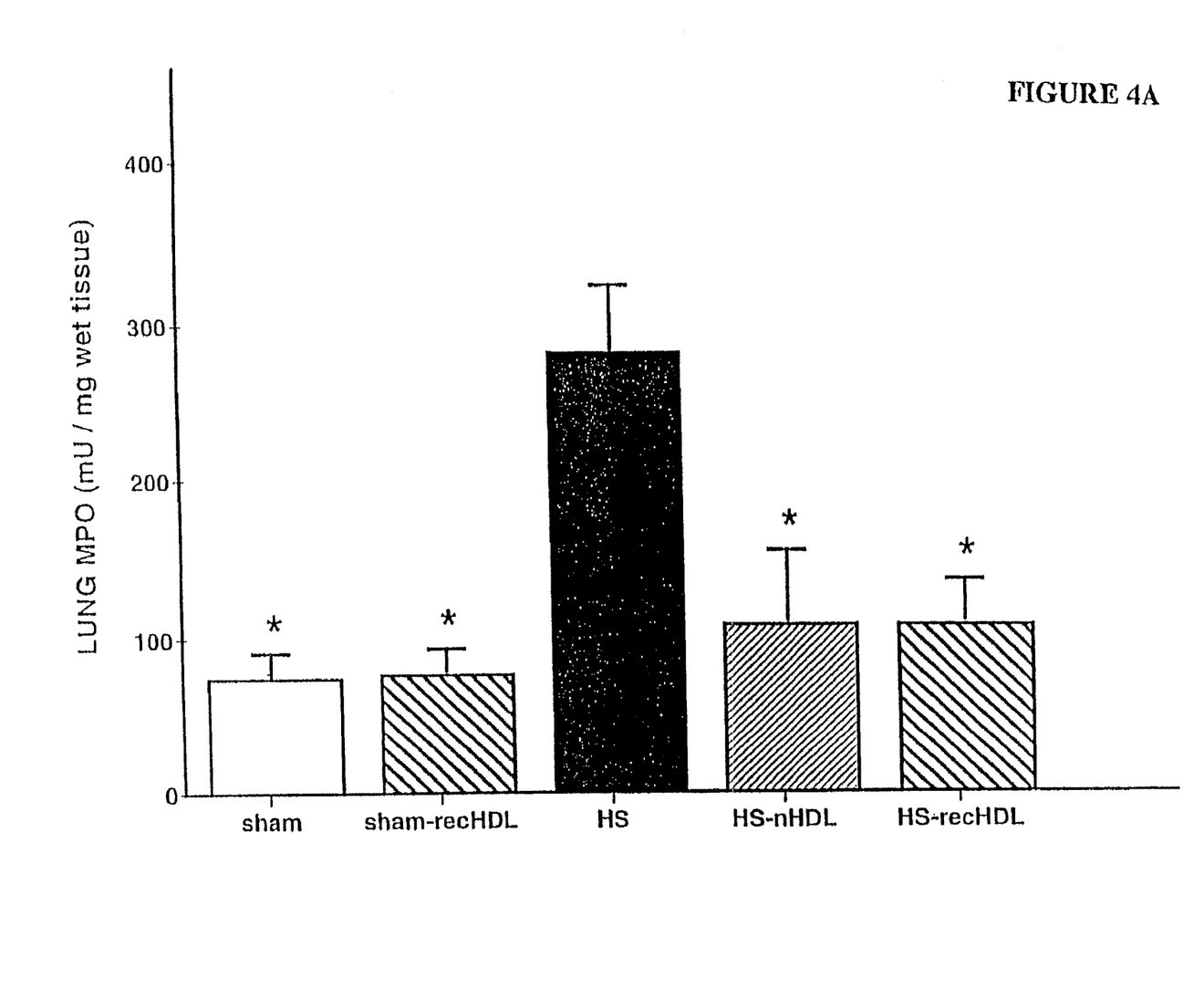
FIG. 4A shows the effect of HDLs on myeloperoxidase (MPO) levels in the lung, as a measure of neutrophil activation.
Figure 4B:
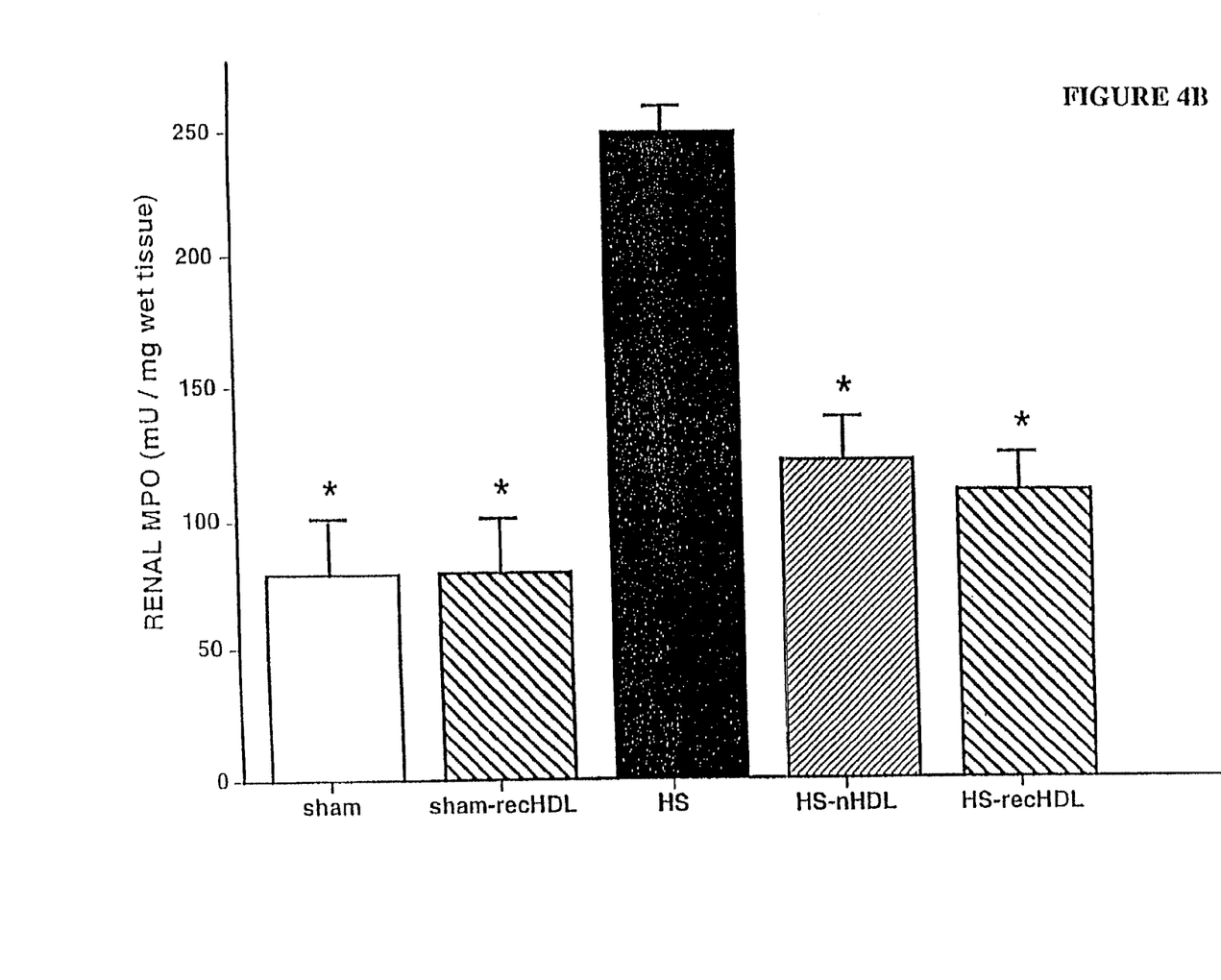
FIG. 4B shows the effect of HDLs on MPO levels in the kidney.

FIG. 4: Graph showing the effect of HDLs on myeloperoxidase (MPO) levels in (A) lung or (B) kidney, as a measure of neutrophil activation. Values represent mean and SEM, n=9; *p<0.05 when compared to haemorrhagic shock (HS).

The ability of HDLs to inhibit the expression of adhesion molecules in this model is strongly supported by the serum data and histology. We further investigated the ability of HDLs to inhibit neutrophil infiltration by measuring the MPO levels in lung (FIG. 4A) and kidney (FIG. 4B). When compared to tissues obtained from sham-operated rats, rats subjected to haemorrhage and resuscitation (solid bars) show an increase in tissue MPO activity. This was reduced in rats which had been treated with either nHDLs or recHDLs prior to resuscitation with shed blood.

HDLs Reduced Malondialdehyde Levels in Lungs and Kidneys Following Haemorrhage and Resuscitation.

Determination of malondialdehyde. Malondialdehyde (MDA) levels in the lung and kidney were determined as an indicator of lipid peroxidation. Tissues were homogenised in 1.15% KCl solution. An aliauot (100 µl) of the homogenate was added to a reaction mixture containing 200 µl 8.1% SDS, 1500 µl 20% acetic acid (pH 3.5), 1500 µl 0.8% thiobarbituric acid and 700 µl distilled water. Samples were then boiled for 1 hour at 95° C. and centrifuged 3,000×g for 10 min. The absorbance of the supernatant was measured spectrophotometrically at 650 nm.

Figure 5A:
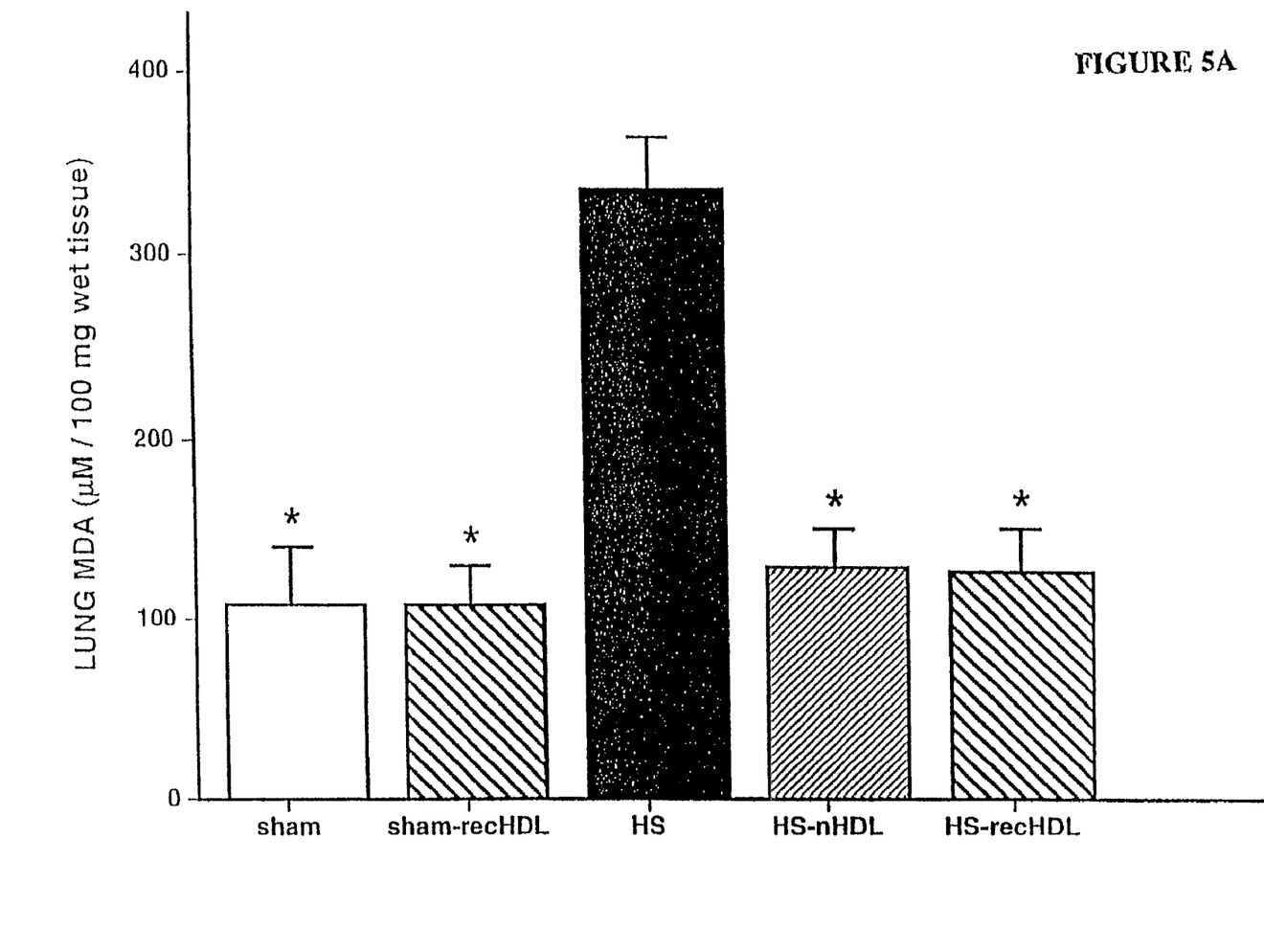
FIG. 5A shows the effect of HDLs on the level of malonialdehyde (MAD) in the lung.
Figure 5B:
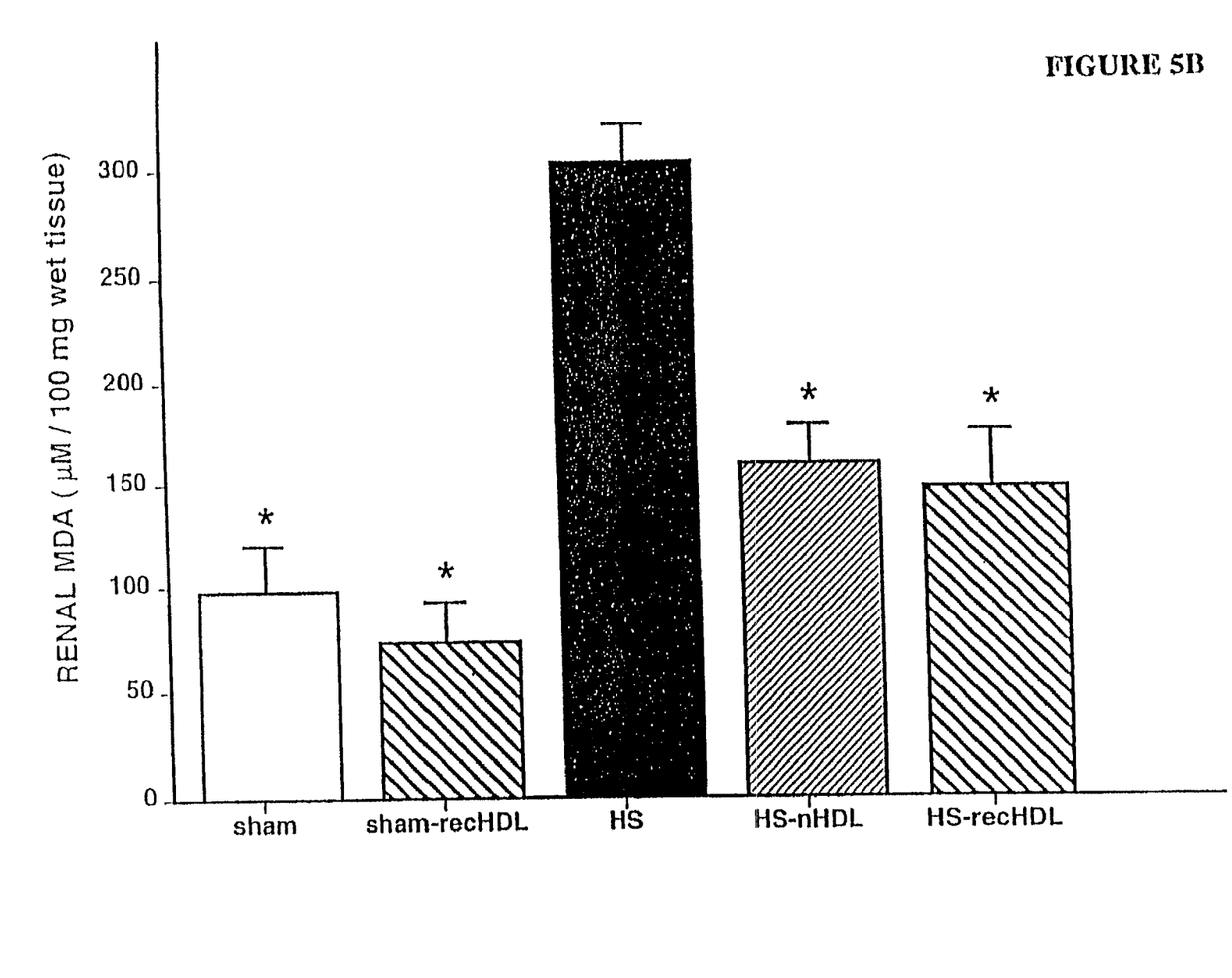
FIG. 5B shows the effect of HDLs on the level of malonialdehyde in the kidney.

FIG. 5: Bar graph showing the effect of HDLs on the level of malondialdehyde (MAD) in lung (A) and (B) kidney, as a measure of the anti-oxidant properties of HDLs. Values represent mean and SEM, n=9; *p,0.05 when compared to haemorrhagic shock (HS).

HDLs have been shown to have anti-oxidant properties. The ability of HDLs to influence the MDA levels in lung (FIG. 5A) and kidney (FIG. 5B) was investigated. When compared to tissues obtained from sham-operated rats, rats subjects to haemorrhage and resuscitation (solid bars) showed a marked increase in tissue MDA activity. This activity was reduced in rats which had been treated with either nHDLs or recHDLs prior to resuscitation [HS-nHDL, HS-recHDL].

In conclusion, administration of recHDL and nHDL attenuates the renal, liver and pancreatic dysfunction following haemorrhagic shock.

Experiment 2

This experiment demonstrates which components of the effective therapeutic agent (HDL) are responsible for protection against haemorrhagic shock; in this experiment, the ability of native HDL to inhibit cytokine-induced adhesion molecule expression on endothelial cells is compared with the ability of lipid-free apo A-I protein or protein-free lipid vesicles.

Cell culture: Human umbilical vein-derived endothelial cells (HUVEC) and human umbilical-derived artery endothelial cells (HUAEC) (Cockerill G. W, Meyer G, Noack L. Vadas M A, Gamble J. R. Lab. Invest. 71: 497–509.1994) were grown on gelatin-coated tissue culture flasks (Costar, High Wycombe, Bucks, UK) in medium 199 with Earle's salts (Gibco, Paisley, Scotland) supplemented with 20% foetal calf serum (FCS) (Gibco, Australia), 20 mM HEPES, 2 mM glutamine, 1 mM sodium pyruvate, non-essential amino acids, penicillin and streptomycin, 50 µg/ml endothelial cell growth supplement (Sigma, Dorset, UK) and 50 µg/ml heparin (normal growth medium).

Flow cytometry: Cells were plated at $1 \times 10^5$ cells/30 mm well and incubated overnight at 37° C. in 5% $CO_2$. Confluent monolayer cultures were then incubated (at concentrations indicated) for 19 hours with either, phosphate buffered saline (PBS) (vehicle control), native HDL, free apo A-I, phospholipid vesicles or discoidal HDL prepared with only apo A-I or apo A-II. Following these treatments the cells were washed gently in complete medium and TNFα (Miles Scientific) was added at 10 ng/ml. Cells were then stained at 4 hours post stimulation in the following manner. Cells were washed in serum free medium and 200 µl anti-E-selectin (1,2B6) was added for 1 hour at 37° C. Cells were then washed in phosphate buffered saline (PBS) containing 5% newborn calf serum, 0.02% sodium azide, and 200 µl of fluorescein isothiocyanate-conjugated secondary antibody added for 1 hour at 37° C. Cells were then washed three times in PBS and trypsinised, then centrifuged to form a pellet. The pellet was then resuspended in 2.5% formaldehyde in PBS containing 2% glucose and 0.02% azide and analyzed in a Coulter Epics Profile II flow cytometer.

Figure 6:
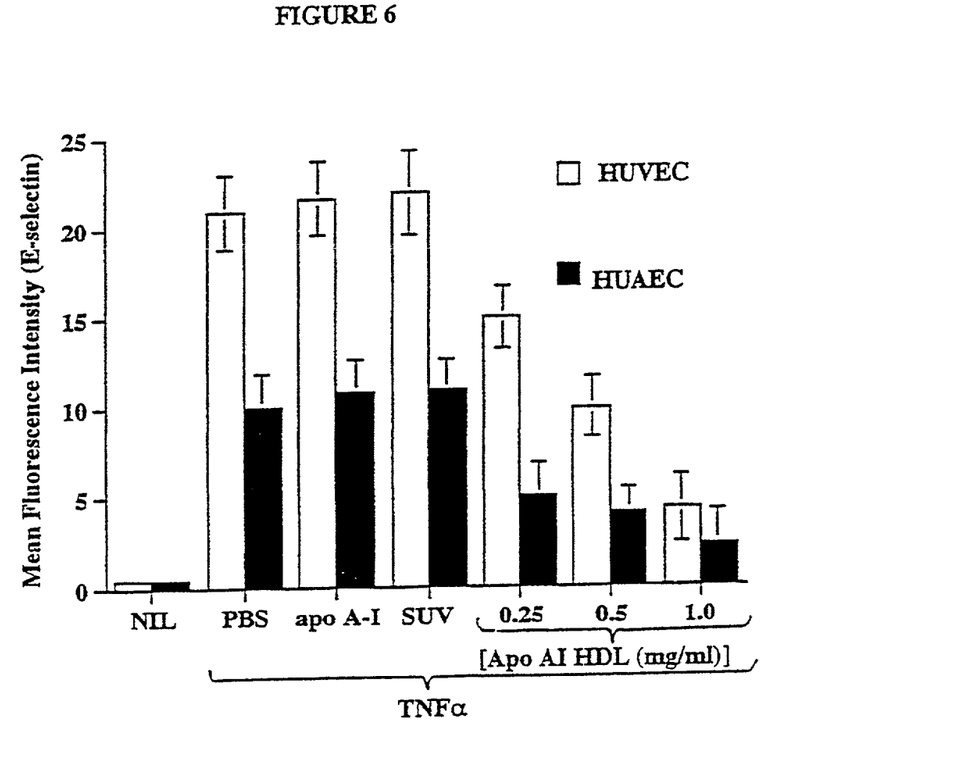
FIG. 6 shows a graph of mean fluorescence intensity (dependent on inhibition of E-selectin), as described below.

FIG. 6 shows that neither free apo A-I nor unilamellar vesicles (SUV) were able to inhibit TNFα-induced expression of E-selectin. This suggests that Apo A-I, the most abundant apolipoprotein in HDL, must be in a lipid particle in order to mediate inhibition of cytokine-induced adhesion molecule expression in endothelial cells. Both umbilical-derived venous (HUVEC) and arterial (HUAEC) endothelial cells were able to support the dose-dependent inhibition of cytokine-induced E-selectin expression by HDL (as shown by the decrease in intensity with increase of apo AI HDL from 0.25 to 11.0 mg/ml).

The therapeutic action of HDL is afforded by the apolipoprotein presented in a lipid particle, and cannot be mimicked by the whole protein alone, or lipid alone.

Experiment 3

To determine the efficacy of reconstituted discoidal HDLs particles containing either of the most abundant apolipoproteins (apo A-I or apo A-II), comparison of the ability of these particles to inhibit cytokine-induced adhesion molecule expression on HUVEC and HUAEC was carried out.

Cell culture: Human umbilical vein-derived endothelial cells (HUVEC) and human umbilical-derived artery endothelial cells (HUAEC) (Cockerill et al., 19994) were grown on gelatin-coated tissue culture flasks (Costar, High Wycombe, Bucks, UK) in medium 199 with Earle's salts (Gibco, Paisley, Scotland), supplemented with 20% foetal calf serum (FCS) (Gibco, Australia), 20 mM HEPES, 2 mM glutamine, 1 mM sodium pyruvate, nonessential amino acids, penicillin and streptomycin, 50 µg/ml endothelial cell growth supplement (Sigma, Dorset, UK) and 50 µg/ml heparin (normal growth medium).

Flow cytometry: Cells were plated at $1\times10^5$ cells/30 mm well and incubated overnight at 37° C. in 5% $CO_2$. Confluent monolayer cultures were then incubated (at concentrations indicated) for 19 hours with either reconstituted discoidal HDL prepared with only apo A-I or apo A-II. Following these treatments the cells were washed gently in complete medium and TNFα (Miles Scientific) was added at 10 ng/ml. Cells were then stained at 4 hours post stimulation in the following manner. Cells were washed in serum free medium and 200 µl anti-E-selectin (1.2B6) was added for 1 hour at 37° C. Cells were then washed in phosphate buffered saline (PBS) containing 5% newborn calf serum, 0.02% sodium azide, and 200 µl of fluorescein isothiocyanate-conjugated secondary antibody added for 1 hour at 37° C. Cells were then washed three time in PBS and trypsinised. The pellet was then resuspended in 2.5% formaldehyde in PBS containing 2% glucose and 0.02% azide and analyzed in a Coulter Epics Profile II flow cytometer.

Preparation of Reconstituted HDL Particles: Discoidal reconstituted A-I HDLs were prepared by the cholate dialysis method from egg yolk phosphatidylcholine, unesterified cholesterol, and apo A-I/apo A-II (Matz C E, Jonas A. Micellar complexes of human apolipoprotein A-I with phosphatidycholines and cholesterol prepared from cholate-lipid dispersion. *J. Biol. Chem.* 1982; 257; 4535–4540). Egg yolk phosphatidycholine, unesterified cholesterol and sodium cholate were obtained from Sigma and used without further purification. Particle size was measured by nondenaturing gradient gel electrophoresis, and concentration of apo A-I and apo A-II was measured immunoturbidimetrically.

Figure 7A:
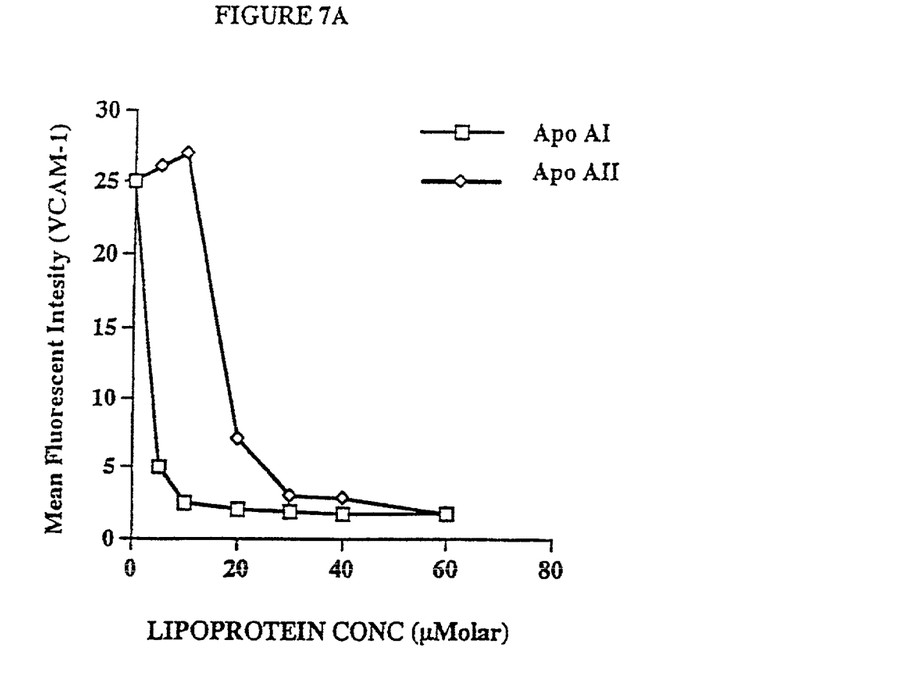
FIG. 7A shows a graph of mean fluorescence intensity of HUVEC (veinous EC) against concentration of lipoproteins apo A-I and apo A-II for experiment 3, below.
Figure 7B:
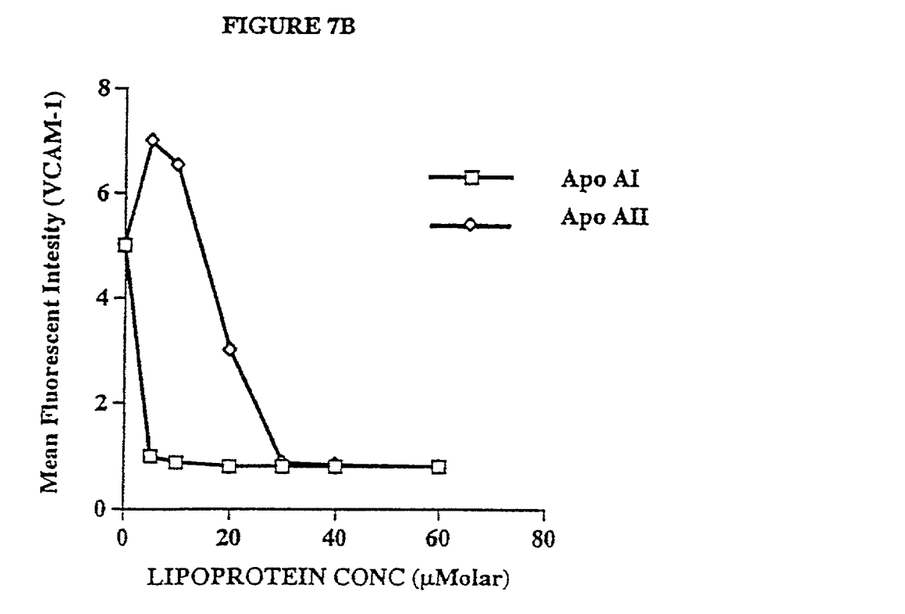
FIG. 7B shows a graph of mean fluorescence intensity of HUAEC (arterial EC) against concentration of lipoprotein apo A-I and apo A-II for experiment 3, below.

Results: Discoidal reconstituted HDL particles containing either apo A-I (open squares) or apo A-II (closed squares), as the sole protein, were able to inhibit TNFα-induced expression of both arterial and venous endothelial cells VCAM-1. FIGS. 7a (HUVEC) and 7b (HuAEC) show reconstituted HDL containing apo A-I, as the sole proteins, having a t1/2 max of approximately 3 µMolar, whilst reconstituted HDL containing apo A-II as the sole protein has a give five-fold greater t1/2 max of 15 µMolar.

Conclusion: The therapeutic action of HDL can be mimicked using either apo A-I or apo A-II in reconstituted lipoprotein particle.

What is claimed is:

1. A method of treatment of organ dysfunction following haemorrhagic shock in a human patient which comprises the step of administering to the patient high density lipoprotein and/or a peptide or protein of the sequence of apo A-I or apo A-II or a peptide or protein functionally homologous to the active portions of apo A-I or apo A-II in pharmaceutically acceptable form.

2. A method according to claim 1 in which the medicament is for the treatment of end-stage organ injury or failure.

3. A method according to claim 2 in which the high density lipoprotein is reconstituted HDL.

4. A method according to claim 2 in which the high density lipoprotein is reconstituted HDL.

5. A method according to claim 1 in which the high density lipoprotein is native HDL.

6. A method according to claim 2 in which the high density lipoprotein is native HDL.

7. A method according to claim 1 in which high density lipoprotein is administered to the patient.

8. A method according to claim 2 in which high density lipoprotein is administered to the patient.

* * * * *